United States Patent
Zhang et al.

(10) Patent No.: US 8,991,241 B1
(45) Date of Patent: Mar. 31, 2015

(54) GAS TURBINE COMPONENT MONITORING

(71) Applicant: General Electric Company, Schenectady, NY (US)

(72) Inventors: Liming Zhang, Greer, SC (US); Jere Allen Johnson, Greenville, SC (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 14/067,136

(22) Filed: Oct. 30, 2013

(51) Int. Cl.
*G01M 15/00* (2006.01)
*G01M 15/14* (2006.01)

(52) U.S. Cl.
CPC .................................. *G01M 15/14* (2013.01)
USPC ....................................................... 73/112.01

(58) Field of Classification Search
USPC ....................................................... 73/112.01
See application file for complete search history.

(56) References Cited

U.S. PATENT DOCUMENTS

| | | | |
|---|---|---|---|
| 4,567,769 A | * | 2/1986 | Barkhoudarian ................ 73/643 |
| 7,302,851 B2 | * | 12/2007 | Czerw et al. .................... 73/620 |
| 2010/0263450 A1 | * | 10/2010 | Bobrek ........................... 73/622 |

FOREIGN PATENT DOCUMENTS

| | | |
|---|---|---|
| JP | 2003014705 A | 1/2003 |
| JP | 2004085347 A | 3/2004 |
| JP | 2004144550 A | 5/2004 |
| JP | 2004212366 A | 7/2004 |
| JP | 2005030846 A | 2/2005 |

* cited by examiner

*Primary Examiner* — Freddie Kirkland, III
(74) *Attorney, Agent, or Firm* — Ernest Cusick; Hoffman Warnick LLC

(57) ABSTRACT

Various embodiments of the invention include methods for monitoring a gas turbine component. In some cases, a method includes: analyzing a gas turbomachine component to detect at least one of a void or a porosity of the gas turbomachine component while maintaining a structural integrity of the gas turbomachine component during the analyzing; and providing instructions to perform a hot isostatic pressing (HIP) process on the gas turbomachine component in response to at least one of detecting the void or detecting that the porosity exceeds a threshold.

18 Claims, 3 Drawing Sheets

US 8,991,241 B1

GAS TURBINE COMPONENT MONITORING

FIELD OF THE INVENTION

The subject matter disclosed herein relates to turbomachine systems. More particularly, the subject matter disclosed herein relates to observation of gas turbomachine systems.

BACKGROUND OF THE INVENTION

Turbomachines, for example, gas turbines and/or steam turbines, operate at high temperatures and pressures, which can cause materials in those turbomachines to degrade, and in some cases, fail. In some turbomachines, e.g., gas turbines, components are maintained (e.g., treated and/or repaired) using a hot isostatic pressing (HIP) process. HIP is a manufacturing process sometimes used to reduce the porosity of a metal (and increase the density of ceramic materials). HIP can improve a material's mechanical properties and workability. HIP involves subjecting a component to an increased temperature and isostatic gas pressure in a high-pressure containment vessel, e.g., using an inert gas.

In some turbomachines, HIP is used to maintain (e.g., treat and/or repair) components such as nozzles and buckets. It may be beneficial to determine the effectiveness of the HIP process on the component. Conventionally, in order to determine the effectiveness of the HIP process on the component, destructive testing is used to determine the creep void or porosity of the component before and after the HIP process. This destructive testing can be expensive and time-consuming. Additionally, in some cases, the destructive testing can require sending the component to an external vendor, which can cause delays and concerns regarding control over technology.

BRIEF DESCRIPTION OF THE INVENTION

Various embodiments of the invention include methods for monitoring a gas turbine component. In some cases, a method includes: analyzing a gas turbomachine component to detect at least one of a void or a porosity of the gas turbomachine component while maintaining a structural integrity of the gas turbomachine component during the analyzing; and providing instructions to perform a hot isostatic pressing (HIP) process on the gas turbomachine component in response to at least one of detecting the void or detecting that the porosity exceeds a threshold.

A first aspect of the invention includes a method. The method can include: analyzing a gas turbomachine component to detect at least one of a void or a porosity of the gas turbomachine component while maintaining a structural integrity of the gas turbomachine component during the analyzing; and providing instructions to perform a hot isostatic pressing (HIP) process on the gas turbomachine component in response to at least one of detecting the void or detecting that the porosity exceeds a threshold.

A second aspect of the invention includes a method for monitoring a gas turbomachine component. The method includes: analyzing the gas turbomachine component to detect at least one of a void or a porosity of the gas turbomachine component while maintaining a structural integrity of the gas turbomachine component during the analyzing; comparing the analysis of the gas turbomachine component with a repair criteria threshold for the gas turbomachine component; and providing instructions to perform a hot isostatic pressing (HIP) process on the gas turbomachine component in response to determining that the analysis of the gas turbomachine component exceeds the repair criteria threshold.

A third aspect of the invention includes a method for monitoring a gas turbomachine component. The method can include: analyzing a gas turbomachine component to detect at least one of a void or a porosity of the gas turbomachine component while maintaining a structural integrity of the gas turbomachine component during the analyzing; providing instructions to perform a hot isostatic pressing (HIP) process on the gas turbomachine component in response to at least one of detecting the void or detecting that the porosity exceeds a threshold; categorizing the gas turbomachine component as not requiring the HIP process in response to detecting that the void and the porosity do not exceed the threshold; analyzing the gas turbomachine component after the HIP process in response to performing of the HIP process on the gas turbomachine component; and determining an effectiveness of the HIP process by comparing the analyzing of the gas turbomachine component to detect at least one of a void or porosity with the analyzing of the gas turbomachine component after the HIP process.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
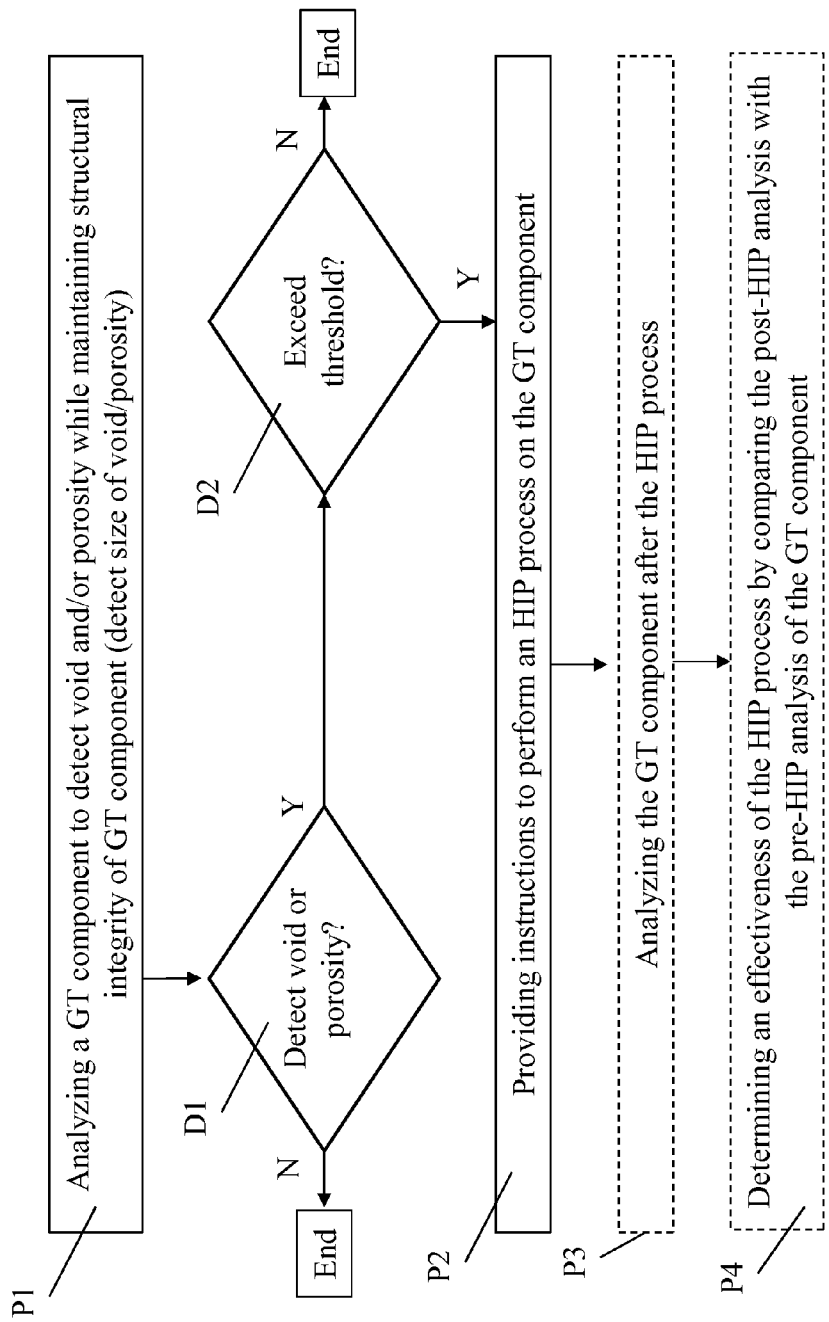
FIG. 1 shows a flow diagram illustrating a method performed according to various embodiments of the invention.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, the subject matter disclosed herein relates to turbomachine systems. More particularly, the subject matter disclosed herein relates to methods for observing gas turbomachine components, e.g., repair of gas turbomachine components.

As noted herein, in some turbomachines, hot isostatic pressing (HIP) is used to maintain (e.g., treat and/or repair) components such as nozzles and buckets. It may be beneficial to determine the effectiveness of the HIP process on the component. Conventionally, in order to determine the effectiveness of the HIP process on the component, destructive testing is used to determine the creep void or porosity of the component before and after the HIP process. This destructive testing can be expensive and time-consuming. Additionally, in some cases, the destructive testing can require sending the component to an external vendor, which can cause delays and concerns regarding proprietary technology control.

In contrast to conventional approaches, various embodiments of the invention include approaches to analyze an HIP process on one or more turbomachine components (e.g., a gas turbomachine component). In various embodiments, the system utilizes a detection approach such as computed tomography (CT) and/or microfocus analysis to determine: a)

whether to perform HIP on a component; and/or b) how effective HIP was at maintaining/repairing the component, in the case that HIP is performed. In particular embodiments of the invention, the detection approach can detect whether the component includes one or more creep voids, and whether the creep void(s) is large enough to benefit from HIP repair.

In various embodiments of the invention, the detection approach is performed on-site, that is, at the same physical location as the turbomachine. In some embodiments, the detection is performed in-situ, that is, while the component is within the turbomachine.

Various particular embodiments include a method including: analyzing a gas turbomachine component to detect at least one of a void or a porosity of the gas turbomachine component while maintaining a structural integrity of the gas turbomachine component during the analyzing; and providing instructions to perform a hot isostatic pressing (HIP) process on the gas turbomachine component in response to at least one of detecting the void or detecting that the porosity exceeds a threshold.

Various additional particular embodiments include a method for monitoring a gas turbomachine component. The method can include: analyzing the gas turbomachine component to detect at least one of a void or a porosity of the gas turbomachine component while maintaining a structural integrity of the gas turbomachine component during the analyzing; comparing the analysis of the gas turbomachine component with a repair criteria threshold for the gas turbomachine component; and providing instructions to perform a hot isostatic pressing (HIP) process on the gas turbomachine component in response to determining that the analysis of the gas turbomachine component exceeds the repair criteria threshold.

Other particular embodiments include a method for analyzing a gas turbomachine component. The method can include: analyzing a gas turbomachine component to detect at least one of a void or a porosity (and in some cases, a total volume of the void or porosity) of the gas turbomachine component while maintaining a structural integrity of the gas turbomachine component during the analyzing; providing instructions to perform a hot isostatic pressing (HIP) process on the gas turbomachine component in response to at least one of detecting the void or detecting that the porosity exceeds a threshold; categorizing the gas turbomachine component as not requiring the HIP process in response to detecting that the void and the porosity do not exceed the threshold; analyzing the gas turbomachine component after the HIP process in response to performing of the HIP process on the gas turbomachine component; and determining an effectiveness of the HIP process by comparing the analyzing of the gas turbomachine component to detect at least one of a void or porosity with the analyzing of the gas turbomachine component after the HIP process.

Various additional embodiments of the invention include a method of monitoring deterioration of a gas turbomachine component by repeatedly monitoring the gas turbomachine component after a series of repair processes (e.g., HIP processes) to determine an effectiveness of long-term repair on one or more voids/porosity.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

FIG. 1 shows a flow diagram illustrating a process of analyzing a turbomachine component (e.g., a gas turbomachine component) according to various embodiments of the invention. One or more of these processes can be performed, e.g., by at least one computing device, as described herein. In other cases, one or more of these processes can be performed according to a computer-implemented method. In still other embodiments, one or more of these processes can be performed by executing computer program code on at least one computing device, causing the at least one computing device to perform a process, e.g., analyzing. In general, the process can include the following sub-processes:

Process P1: analyzing a gas turbomachine (GT) component to detect at least one of a void or a porosity of the GT component while maintaining a structural integrity of the GT component during the analyzing. That is, analyzing as used herein refers to non-destructively analyzing a GT component to determine one or more physical characteristics of that component. During the analyzing, the GT component remains in tact, that is, substantially physically undisturbed. In various embodiments, the GT component includes a creep-limited component for use in a GT, for example, at least one of a GT nozzle or a GT bucket. The GT component can also include couplings or portions of rotor diaphragm and/or casing segments. In some embodiments, the analyzing includes performing a computed tomography (CT) scan of the GT component. In other embodiments, the analyzing includes performing a microfocus analysis of the GT component. In some cases, the void includes a dimensional change in the GT component as compared with a previously established dimensional value of the gas turbomachine component, and the analyzing includes determining a size of the void.

Decision D1: Is a void or porosity detected? If No, End. If Yes, proceed to Decision D2.

Decision D2: Does the void exceed a repair criteria threshold void level (e.g., size) and/or the porosity exceed a repair criteria threshold level? As described herein, according to various embodiments, the process can further include determining a total volume of the void and/or porosity. As described herein, a detection system 150 (e.g., CT system, a vision system using laser-based detection, infra-red, etc.) can be used to determine a size of the void or porosity, and in some cases, can detect the presence of the void or porosity (process P1). According to various embodiments, if a void or porosity is detected, its detected size is compared with a threshold void/porosity size based upon sample data. If No to decision D2, End. If Yes, proceed to process P2.

Process P2: Providing instructions to perform a hot isostatic pressing (HIP) process on the GT component (in response to determining the void and/or porosity exceeds respective threshold level. In various embodiments, the HIP process is performed off-site, e.g., at a physical location distinct from a location of a gas turbomachine (GT) for housing the GT component. In some cases, the analyzing includes detecting a size of the at least one of the void or the porosity. The analyzing can be performed on site, e.g., at a same physical location as the GT for housing the GT component. In more particular embodiments, the analyzing is performed in situ within the GT.

Process P3 (optional post-process): analyzing the gas turbomachine component after the HIP process. This can include utilizing the detection system 150 (e.g., CT data) to determine whether the void and/or porosity still exists, and if so, its size/volume.

Process P4 (optional post-process): determining an effectiveness of the HIP process by comparing the analyzing of the gas turbomachine component to detect at least one of a void or porosity with the analyzing of the gas turbomachine component after the HIP process. In some cases, this can include comparing the CT data about the size of the void/porosity, obtained at the detection system 150, with a known maximum acceptable void size based upon specifications of the gas turbomachine component. If the CT data about the size of the void/porosity indicates that the post-HIP process component has a void/porosity size that exceeds the known maximum acceptable void size, the process can include indicating that the HIP process was ineffective.

In various embodiments, the void status of the gas turbomachine component can be recorded, e.g., after a first HIP process, and that recorded void status can be used to determine an effectiveness of subsequent HIP processes on the component. This void status data can also be used to track deterioration of the gas turbomachine component over time and/or over repair intervals (e.g., HIP process intervals).

In various embodiments, Processes P1-P4 (including Decisions D1-D2) can be iterated (repeated) periodically (e.g., according to schedule of x times per y period, and/or continuously) in order to monitor one or more GT components. In some cases, processes P1-P4 can be repeated, for example, for a set of GT components.

Figure 2:
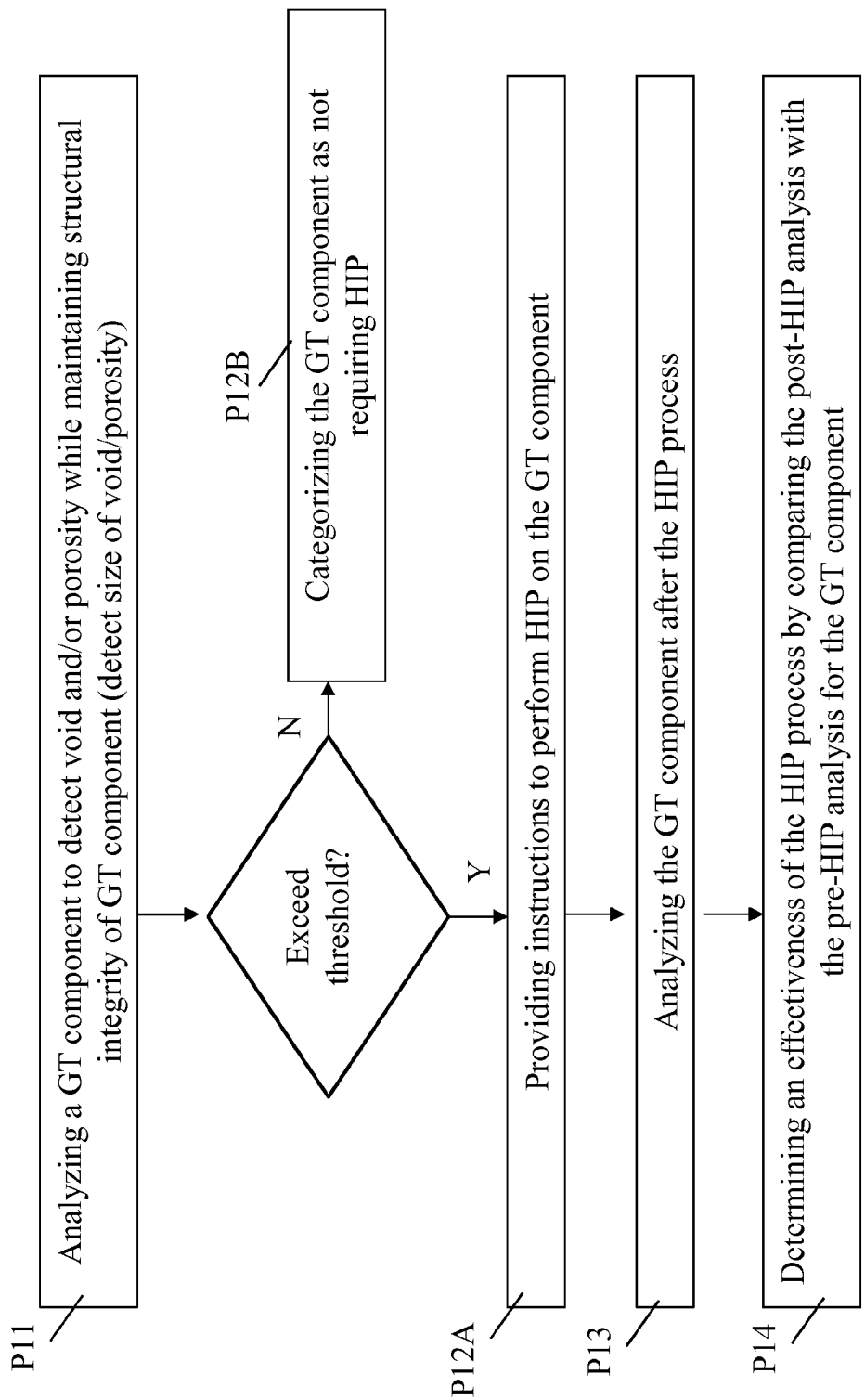
FIG. 2 shows a flow diagram illustrating a method performed to particular embodiments of the invention.

Various additional embodiments include methods of monitoring a GT component. FIG. 2 shows a flow diagram illustrating a process of analyzing a turbomachine component (e.g., a GT component) according to various embodiments of the invention. One or more of these processes can be performed, e.g., by at least one computing device, as described herein. In other cases, one or more of these processes can be performed according to a computer-implemented method. In still other embodiments, one or more of these processes can be performed by executing computer program code on at least one computing device, causing the at least one computing device to perform a process, e.g., analyzing. In general, the process can include the following sub-processes:

Process P11: Analyzing a GT component to detect at least one of a void or a porosity of the GT component while maintaining a structural integrity of the GT component (during the analyzing).

Process P12A: providing instructions to perform a hot isostatic pressing (HIP) process on the gas turbomachine component in response to at least one of detecting the void or detecting that the porosity exceeds a threshold;

Process P12B: categorizing the gas turbomachine component as not requiring the HIP process in response to detecting that the void and the porosity do not exceed the threshold;

P13 (following process P12A): analyzing the gas turbomachine component after the HIP process in response to performing of the HIP process on the gas turbomachine component; and Process P14 (following process P13): determining an effectiveness of the HIP process by comparing the analyzing of the gas turbomachine component to detect at least one of a void or porosity with the analyzing of the gas turbomachine component after the HIP process.

It is understood that in the flow diagrams shown and described herein, other processes may be performed while not being shown, and the order of processes can be rearranged according to various embodiments. Additionally, intermediate processes may be performed between one or more described processes. The flow of processes shown and described herein is not to be construed as limiting of the various embodiments.

Figure 3:
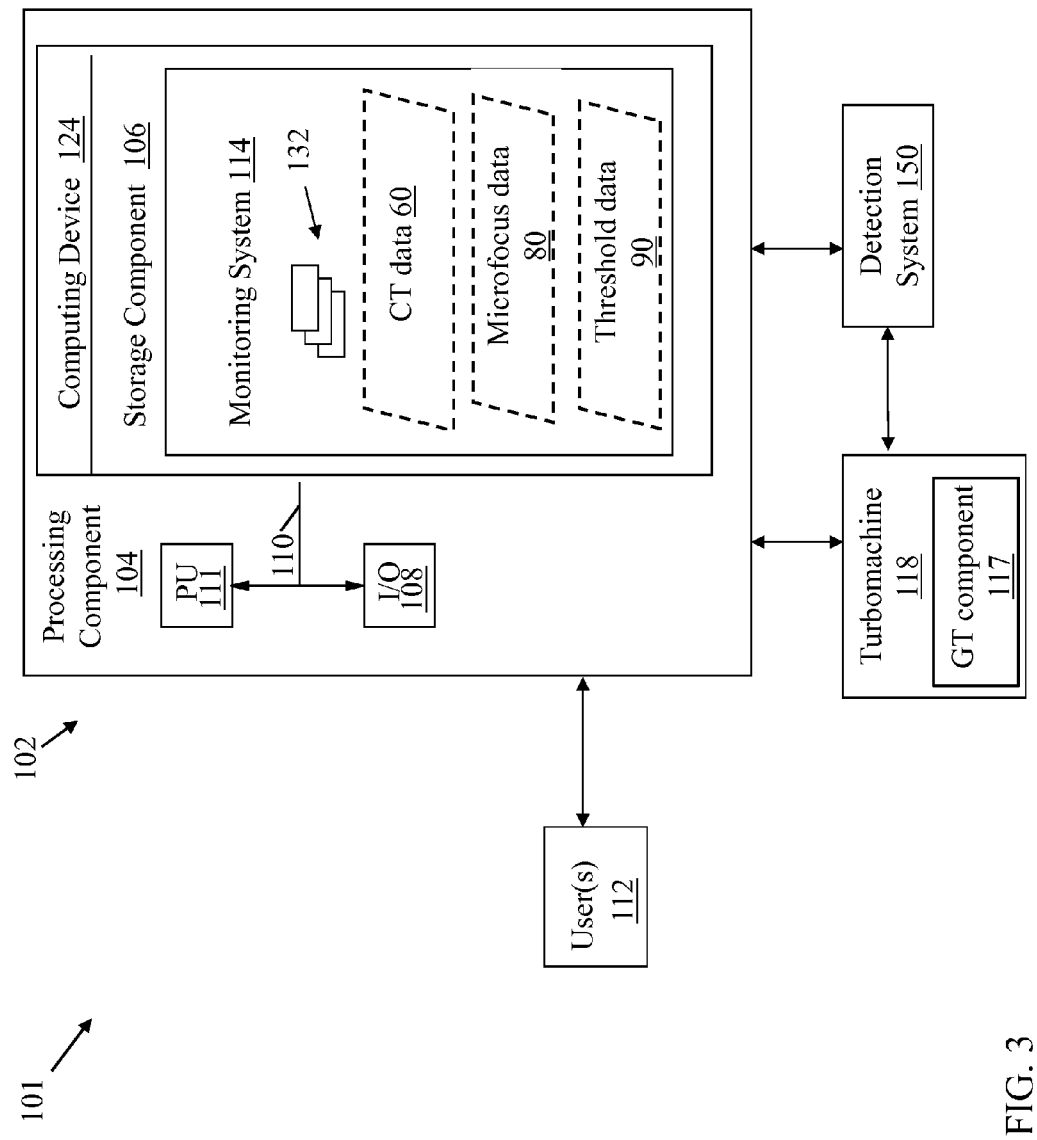
FIG. 3 shows an environment including a system according to various embodiments of the invention.

FIG. 3 shows an illustrative environment 101 including a monitoring system 114, for performing the functions described herein according to various embodiments of the invention. To this extent, the environment 101 includes a computer system 102 that can perform one or more processes described herein in order to monitor a GT component 117, e.g., from a turbomachine 118. In particular, the computer system 102 is shown as including the monitoring system 114, which makes computer system 102 operable to monitor a GT component 117 by performing any/all of the processes described herein and implementing any/all of the embodiments described herein.

The computer system 102 is shown including a computing device 124, which can include a processing component 104 (e.g., one or more processors, or processing units (PUs) 111), a storage component 106 (e.g., a storage hierarchy), an input/output (I/O) component 108 (e.g., one or more I/O interfaces and/or devices), and a communications pathway 110. In general, the processing component 104 executes program code, such as the monitoring system 114, which is at least partially fixed in the storage component 106. While executing program code, the processing component 104 can process data, which can result in reading and/or writing transformed data from/to the storage component 106 and/or the I/O component 108 for further processing. The pathway 110 provides a communications link between each of the components in the computer system 102. The I/O component 108 can comprise one or more human I/O devices, which enable a user (e.g., a human and/or computerized user) 112 to interact with the computer system 102 and/or one or more communications devices to enable the system user 112 to communicate with the computer system 102 using any type of communications link. To this extent, the monitoring system 114 can manage a set of interfaces (e.g., graphical user interface(s), application program interface, etc.) that enable human and/or system users 112 to interact with the monitoring system 114. Further, the monitoring system 114 can manage (e.g., store, retrieve, create, manipulate, organize, present, etc.) data, such as computed tomography (CT) data 60 (e.g., data about the presence or absence of voids in the GT component 117, size of voids in the GT component 117, creep measurement data about the GT component 117, etc., obtained by detection system 150), microfocus data 80 (data about the presence or absence of voids in the GT component 117, size of voids in the GT component 117, creep measurement data about the GT component 117, etc., obtained by detection system 150) and/or threshold data 90 (e.g., data about one or more thresholds, e.g., repair criteria threshold(s), void threshold(s), creep threshold(s), etc.) using any solution. The monitoring system 114 can additionally communicate with a turbomachine 118 and/or the detection system 150 (e.g., a CT system and/or microfocus system) via wireless and/or hardwired means.

In any event, the computer system 102 can comprise one or more general purpose computing articles of manufacture (e.g., computing devices) capable of executing program code, such as the monitoring system 114, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the monitoring system 114 can be embodied as any combination of system software and/or application software. It is further understood that the monitoring system 114 can be implemented in a cloud-based computing environment, where one or more processes are performed at distinct computing devices (e.g., a plurality of computing devices 124), where one or more of those distinct computing devices may contain only some of the components shown and described with respect to the computing device 124 of FIG. 3.

Further, the monitoring system 114 can be implemented using a set of modules 132. In this case, a module 132 can enable the computer system 102 to perform a set of tasks used by the monitoring system 114, and can be separately developed and/or implemented apart from other portions of the monitoring system 114. As used herein, the term "component" means any configuration of hardware, with or without software, which implements the functionality described in conjunction therewith using any solution, while the term "module" means program code that enables the computer system 102 to implement the functionality described in conjunction therewith using any solution. When fixed in a storage component 106 of a computer system 102 that includes a processing component 104, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 102.

When the computer system 102 comprises multiple computing devices, each computing device may have only a portion of monitoring system 114 fixed thereon (e.g., one or more modules 132). However, it is understood that the computer system 102 and monitoring system 114 are only representative of various possible equivalent computer systems that may perform a process described herein. To this extent, in other embodiments, the functionality provided by the computer system 102 and monitoring system 114 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 102 includes multiple computing devices 124, the computing devices can communicate over any type of communications link. Further, while performing a process described herein, the computer system 102 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 102 can obtain or provide data, such as CT data 60, microfocus data 80 and/or threshold data 90 using any solution. The computer system 102 can generate CT data 60, microfocus data 80 and/or threshold data 90, from one or more data stores, receive CT data 60, microfocus data 80 and/or threshold data 90, from another system such as the turbomachine 118, detection system 150 and/or the user 112, send CT data 60, microfocus data 80 and/or threshold data 90 to another system, etc.

While shown and described herein as a method and system for monitoring a GT component 117, it is understood that aspects of the invention further provide various alternative embodiments. For example, in one embodiment, the invention provides a computer program fixed in at least one computer-readable medium, which when executed, enables a computer system to monitor a GT component 117. To this extent, the computer-readable medium includes program code, such as the monitoring system 114 (FIG. 3), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the monitoring system 114 (FIG. 3), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of monitoring a lubrication oil In this case, a computer system, such as the computer system 102 (FIG. 3), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the various embodiments of the invention, including, e.g., the monitoring system 114, is to monitor a component in a turbomachine 118 (e.g., a GT component 117).

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method comprising:
   analyzing a gas turbomachine component to detect at least one of a void or a porosity of the gas turbomachine component while maintaining a structural integrity of the gas turbomachine component during the analyzing, wherein the analyzing includes performing a computed tomography (CT) scan of the gas turbomachine component; and
   providing instructions to perform a hot isostatic pressing (HIP) process on the gas turbomachine component in response to at least one of detecting the void or detecting that the porosity exceeds a threshold.

2. The method of claim 1, further comprising analyzing the gas turbomachine component after the HIP process.

3. The method of claim 2, further comprising determining an effectiveness of the HIP process by comparing the analyzing of the gas turbomachine component to detect at least one of a void or porosity with the analyzing of the gas turbomachine component after the HIP process.

4. The method of claim 1, wherein the gas turbomachine component includes a creep-limited component for use in a gas turbomachine.

5. The method of claim 4, wherein the creep-limited component includes at least one of a nozzle or a bucket.

6. The method of claim 1, wherein the analyzing includes performing a microfocus analysis of the gas turbomachine component.

7. The method of claim 1, wherein the analyzing is performed at a same physical location as a gas turbomachine for housing the gas turbomachine component.

8. The method of claim 7, wherein the analyzing is performed in situ within the gas turbomachine.

9. The method of claim 1, wherein the void includes a dimensional change in the gas turbomachine component as compared with a previously established dimensional value of the gas turbomachine component, and wherein the analyzing includes determining a size of the void.

10. A method for monitoring a gas turbomachine component, the method comprising:
    analyzing the gas turbomachine component to detect at least one of a void or a porosity of the gas turbomachine component while maintaining a structural integrity of the gas turbomachine component during the analyzing, wherein the analyzing includes performing a computed tomography (CT) scan of the gas turbomachine component;
    comparing the analysis of the gas turbomachine component with a repair criteria threshold for the gas turbomachine component; and
    providing instructions to perform a hot isostatic pressing (HIP) process on the gas turbomachine component in response to determining that the analysis of the gas turbomachine component exceeds the repair criteria threshold.

11. The method of claim 10, wherein the analyzing to detect the at least one of the void or the porosity includes detecting a size of the at least one of the void or the porosity.

12. The method of claim 11, wherein the repair criteria threshold is based upon the size of the at least one void or porosity.

13. The method of claim 10, wherein the repair criteria threshold is based upon a presence of at least one creep void or at least one internal crack in the gas turbomachine component.

14. The method of claim 10, wherein the gas turbomachine component includes a creep-limited component for use in a gas turbomachine.

15. The method of claim 14, wherein the creep-limited component includes at least one of a nozzle or a bucket.

16. The method of claim 10, wherein the analyzing includes performing a microfocus analysis of the gas turbomachine component.

17. The method of claim 10, further comprising:
    analyzing the gas turbomachine component after the HIP process; and
    determining an effectiveness of the HIP process by comparing the analyzing of the gas turbomachine component to detect at least one of a void or porosity with the analyzing of the gas turbomachine component after the HIP process.

18. A method for monitoring a gas turbomachine component, the method comprising:
    analyzing a gas turbomachine component to detect at least one of a void or a porosity of the gas turbomachine component while maintaining a structural integrity of the gas turbomachine component during the analyzing, wherein the analyzing includes performing a computed tomography (CT) scan of the gas turbomachine component;
    providing instructions to perform a hot isostatic pressing (HIP) process on the gas turbomachine component in response to at least one of detecting the void or detecting that the porosity exceeds a threshold;
    categorizing the gas turbomachine component as not requiring the HIP process in response to detecting that the void and the porosity do not exceed the threshold;
    analyzing the gas turbomachine component after the HIP process in response to performing of the HIP process on the gas turbomachine component; and
    determining an effectiveness of the HIP process by comparing the analyzing of the gas turbomachine component to detect at least one of a void or porosity with the analyzing of the gas turbomachine component after the HIP process.

* * * * *